United States Patent
Vogt et al.

(10) Patent No.: US 6,596,864 B1
(45) Date of Patent: Jul. 22, 2003

(54) STILBENE BRIGHTENER

(75) Inventors: Uwe Vogt, Monheim (DE); Rolf Brockmann, Bergisch Gladbach (DE); Thomas Roick, Leverkusen (DE); Karl-Rudolf Gassen, Ratingen (DE); Ulrich Feldhues, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,309

(22) PCT Filed: Apr. 25, 2000

(86) PCT No.: PCT/EP00/03685

§ 371 (c)(1),
(2), (4) Date: Oct. 30, 2001

(87) PCT Pub. No.: WO00/68211

PCT Pub. Date: Nov. 16, 2000

(30) Foreign Application Priority Data

May 5, 1999 (DE) .......................... 199 20 784

(51) Int. Cl.$^7$ .......................... C07D 251/52; D06L 3/12
(52) U.S. Cl. .......................... 544/193.2; 252/301.23; 252/8.63; 8/566; 8/190
(58) Field of Search .................. 544/193.2; 252/301.23, 252/8.63

(56) References Cited

U.S. PATENT DOCUMENTS

| | | | |
|---|---|---|---|
| 3,265,654 A | 8/1966 | Glabisch et al. | 260/29.6 |
| 3,525,618 A | 8/1970 | Riehen et al. | 96/75 |
| 5,744,599 A | 4/1998 | Reinehr et al. | 544/193.1 |
| 6,015,504 A | 1/2000 | Reinehr et al. | 252/8.91 |

FOREIGN PATENT DOCUMENTS

| | | |
|---|---|---|
| DE | 20 56 195 | 5/1972 |
| DE | 23 35 570 | 1/1974 |
| EP | 24 380 | 3/1981 |
| EP | 626 374 | 11/1994 |
| EP | 860 437 | 8/1998 |
| GB | 2021193 | 3/1966 |

*Primary Examiner*—Richard L. Raymond
*Assistant Examiner*—Venkataraman Balasubramanian
(74) *Attorney, Agent, or Firm*—Godfried R. Akorli; Diderico van Eyl

(57) ABSTRACT

This invention relates to compounds of the formula (I)

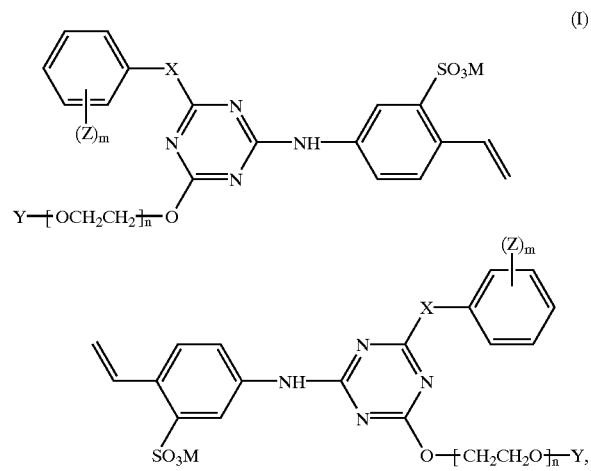

where

Z is $SO_3M$, $COOR^1$, $CONR^1$, $SO_2NHR^1$, $NHCOR^1$, $COR^2$, or CN, where
  $R^1$ is M or $C_1$–$C_3$-alkyl and
  $R^2$ is $C_1$–$C_3$-alkyl or phenyl, X is O or $NR^3$, where
  $R^3$ is hydrogen or $C_1$–$C_4$-alkyl, Y is hydrogen or $C_1$–$C_4$-alkyl, M is hydrogen, an alkali metal cation, or an optionally substituted ammonium ion, n is from 4 to 35, and m is 0, 1 or 2.

9 Claims, No Drawings

STILBENE BRIGHTENER

The invention relates to novel brighteners, a process for their preparation and their use for brightening substrates.

DE-A-2 335 570 discloses stilbene brighteners whose terminal triazinyl radicals are substituted with short-chain polyether alcohols.

EP-A-24 380 discloses stilbene brighteners whose terminal triazinyl radicals are substituted with phenyl-saturated ethylene oxide units.

Surprisingly, there have now been found optical brighteners conforming to the formula (I)

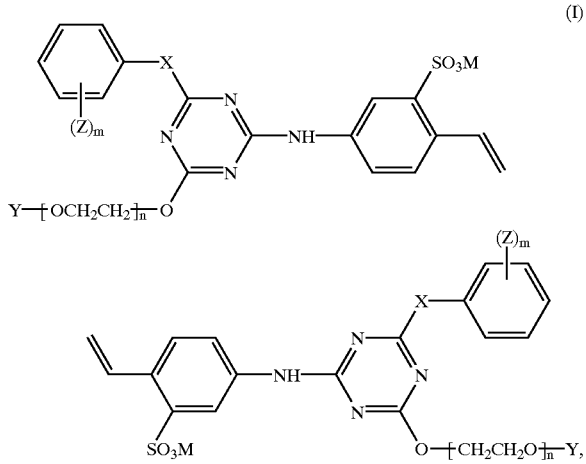

where

Z is $SO_3M$, $COOR^1$, $CONR^1$, $SO_2NHR^1$, $NHCOR^1$, $COR^2$ or CN, where
  $R^1$ is M or $C_1$–$C_3$-alkyl and
  $R^2$ is $C_1$–$C_3$-alkyl or phenyl,
X is O or $NR^3$, where
  $R^3$ is hydrogen or $C_1$–$C_4$-alkyl,
Y is hydrogen or $C_1$–$C_4$-alkyl, especially methyl,
M is hydrogen, an alkali metal cation or an optionally substituted ammonium ion,
n is from 4 to 35, especially from 5 to 25, preferably from 7 to 25 and
m is 0, 1 or 2.

The index n is herein to be understood as a statistical variable and preferably represents the mean.

Preferred brighteners are those in which the radical of the formula

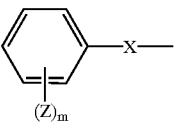

is derived from compounds of the formula (V)

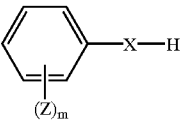

(V)

Preferred compounds of the formula (V) are phenol, phenolsulfonic acid, aniline, sulfanilic acid, dimetanilic acid (2,5-disulfoaniline).

Preferred brighteners of the formula (I) are those where
Z is $SO_3M$,
m is 0, 1 or 2
X is NH,
n is from 4 to 15, especially from 5 to 15, preferably from 7 to 15,
Y is hydrogen and
M is hydrogen, Na, K or a $C_1$–$C_4$-mono-, -di-, -tri- or -tetra-alkanolammonium.

Particularly preferred brighteners of the formula (I) are those where
Z is $SO_3M$,
m is 1,
X is NH,
n is from 4 to 15, especially from 5 to 15, preferably from 7 to 15,
Y is hydrogen and
M is Na or K.

Particularly preferred brighteners of the formula (I) conform to the formula (II)

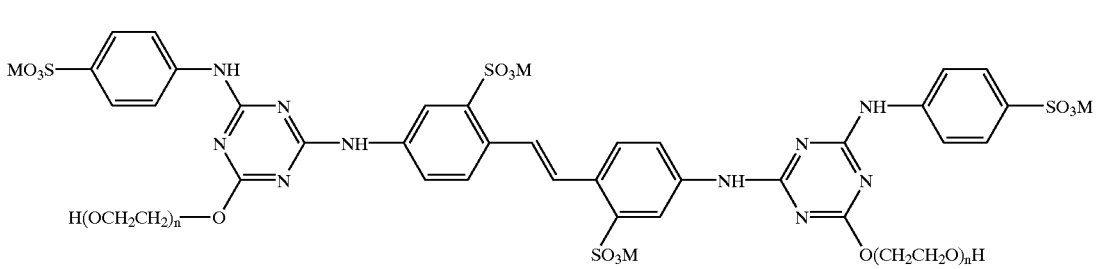

where

M is hydrogen, Na or K and
n is from 4 to 15, preferably from 5 to 15, especially from 7 to 15.

The invention further provides a process for preparing the compounds of the formula (I), which is characterized in that compounds of the formula (III)

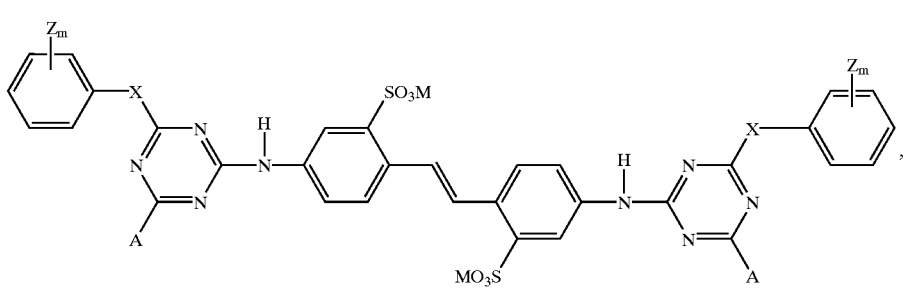

(III)

where

A is Cl or F, especially Cl, are reacted with polyglycols or polyglycol ethers of the general formulae (IV)

where Z, X, Y, m and n are each as defined above.

In a particular embodiment of the process according to the invention, the reaction is effected at a temperature of 20 to 100° C., preferably in the presence of an acid-binding agent, such as for example sodium hydroxide, potassium hydroxide, sodium carbonate or potassium carbonate.

The reaction is generally carried out similarly to the procedure disclosed in DE-2 335 570.

Compounds of the formula (III) are known for example from EP-A-860 437.

Preferred compounds of the formula (IV) are for example polyethylene glycols, especially those where n=4 to 35, especially 4 to 25, preferably 5 to 25, particularly preferably 7 to 25, preferably with an average molecular weight of 200 to 1000 g/mol, especially 200, 300, 400, 600 and 1000 g/mol, and also their corresponding monomethyl ethers.

Particular preference is given to using compounds of the formula (IV) which are polyethylene glycols having average molecular weights of 200 to 600 g/mol.

The compounds of the formula (I) according to the invention are generally prepared using an excess of compounds of the formula (IV). The molar excess of IV, based on III, is preferably 5 to 20 mol. This excess of (IV) can be removed from the end product by diafiltration for example. Preferably, however, the excess stays in the end product, since it has a positive influence on the stability of the liquid formulation and also on the whiteness of the brightened material.

The invention also provides brightener preparations containing the brightener of the formula (I) according to the invention and a polyglycol ether. Preferred polyglycol ethers are those of the formula (IV) where the meanings for Y and n can be independent of those of the formula (I).

Preference is given to those brightener preparations containing

10–25% by weight of brightener of the formula (I)

20–60% by weight of polyglycol ether

15–70% by weight of water.

Salts may be present in addition.

When polyglycol ethers of the formula (IV) are used, polyethylene glycols (PEGs) having molecular weights of 1500 to 6000 g/mol can be used in addition. The latter can be present at 0 to 40% by weight, based on the preparation.

The compounds of the general formula (I) according to the invention are optical brighteners for various substrates. Particularly preferred substrates are those composed of natural cellulose such as cotton, paper and wood materials in fine dispersion or materials composed of regenerated cellulose, of wool or synthetic polyamides. The materials to be optically brightened can be present in a wide variety of processing stages such as raw material, intermediate article or finished article and in a wide variety of processing forms such as for example fibers, threads, wovens, formed-loop knits, webs and also films etc.

The compounds according to the invention can also have laundry detergent added to them. The solid and liquid laundry detergents used can contain the customary ingredients corresponding to the prior art.

The compounds of the invention can further be applied during the resin finishing of fiber materials in conjunction with synthetic resins and synthetic resin precondensates. The crosslinking of the synthetic resins can be carried out over a wide pH range, especially from pH 1 to pH 10, in a conventional manner. Thus, especially the compounds of the formula (I) according to the invention in which Z is $SO_3M$, m is 1 or 2, X is NH, n is from 4 to 15, preferably from 5 to 15, especially from 7 to 15, Y is hydrogen and M is Na or K are suitable for the optical brightening of cellulose materials from acidic crosslinking baths, as is customary for the wash and wear finishing of cellulose fibers.

The compounds according to the invention can further be used for raising the sun protection factor of textile materials. The use of diaminestilbenedisulfonic acid derivatives for raising the sun protection factor of textile materials is known and described for example in EP-A 728 749 (=GB 9 503 474). Suitable for this use are in particular the compounds of the general formula (I) according to the invention where Z represents $COOR^1$, where $R^1$ is $C_1$–$C_3$-alkyl or M, or represents $CONR^1$, $SO_2NHR^1$, $NHCOR^1$, $CO$—$R^3$, where $R^3$ is $C_1$–$C_3$-alkyl or phenyl, or represents CN, m represents 1, X represents NH, n represents from 4 to 15, preferably from 5 to 15, especially from 7 to 15, Y represents hydrogen or methyl, M represents hydrogen, an alkali metal cation or an optionally substituted ammonium ion.

To raise the sun protection factor of textile materials, the textile material can be treated directly with the compounds of the invention, or else the effect is achieved as part of a normal domestic laundering process when the laundry detergent used contains the compound according to the invention.

The brighteners of the formula (I) according to the invention are suitable for brightening paper materials in papermaking, for example cellulose, chemical and mechanical pulp, and for brightening the coating compositions customarily used in the paper industry, specifically for brightening unpigmented but especially pigmented paper materials and coating compositions.

The binders in known coating compositions include polymer dispersions based on copolymers of butadiene-styrene, acrylonitrile-butadiene-styrene, acrylic esters, ethylene-vinyl chloride or ethylene-vinyl acetate or based on homopolymers, such as polyvinyl chloride, polyvinylidene chloride, polyethylene, polyvinyl acetate or polyurethanes. A preferred binder consists of styrene-butyl acrylate or styrene butadiene-acrylic acid interpolymers. Further polymer latices are described, for example, in U.S. Pat. No. 3,265,654.

The coating compositions are customarily pigmented using aluminum silicates, such as china clay and kaolin, also barium sulfate, satin white, titanium dioxide or calcium carbonate (chalk).

The coating compositions according to the invention preferably contain 5 to 70% by weight of a white pigment. The binder is preferably used in an amount such that the solids content of polymeric compound comprises 1 to 30% by weight, preferably 5 to 25% by weight, of the white pigment. The amount of the brightener according to the invention is determined in such a way that the brightener is present in amounts of 0.005 to 1% by weight, especially 0.01 to 0.55% by weight, based on white pigment.

The coating composition according to the invention can be prepared by mixing the components in any order at temperatures of 10 to 100° C., preferably 20 to 80° C. The components also include the customary auxiliaries which can be used to regulate the rheological properties, such as the viscosity or water retention capability, of the coating compositions. Such auxiliaries are for example natural binders, such as starch, casein, protein or gelatin, cellulose ethers, such as carboxyalkylcellulose or hydroxyalkylcellulose, alginic acid, alginates, polyethylene oxide or polyethylene oxide alkyl ethers, interpolymers of ethylene oxide and propylene oxide, polyvinyl alcohol, polyvinylpyrrolidone, water-soluble condensation products of formaldehyde with urea or melamine, polyphosphates or polyacrylic acid salts.

The brighteners of the formula (I) according to the invention are incorporated either into the finished coating composition or into one of the components of the coating composition.

The coating composition according to the invention can be used for coating paper, wood, films, such as for example cellulose, cellulose triacetate, textile materials, etc. Particular preference is given to the application to paper and cardboard and also photopapers.

The coating composition can be applied to the substrate by any conventional method, for example using an air knife, a coating blade, a brush, a roll, a doctor or a rod, and the coating is then dried, for example using an infrared dryer and/or hot air dryer, at substrate surface temperatures in the range from 70 to 200° C., preferably from 90 to 130° C., to a residual moisture content of 3 to 6% by weight.

The coating compositions according to the invention provide coatings notable for an optimum distribution of the optical brighteners across the entire surface and an attendant increase in the whiteness and also for a high lightfastness.

EXAMPLES

Example 1

Preparation of the Compound of the Formula 1

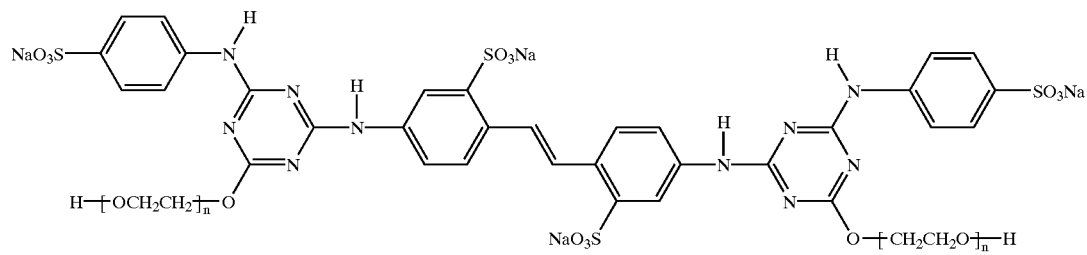

formula 1 n = 8.5

117 g of the compound of the formula formula (2)

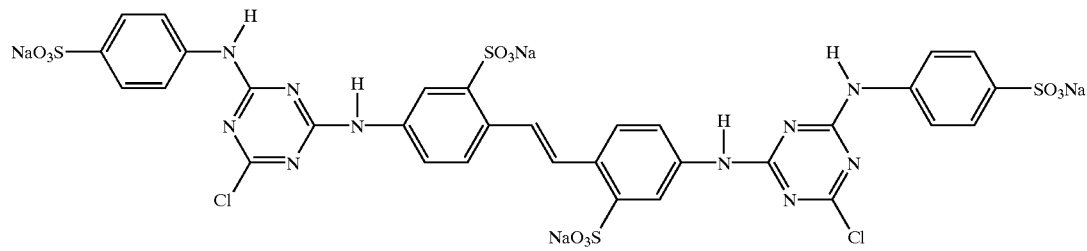

formula 2 are suspended in a mixture of 500 g of polyglycol 400 and 281 g of 7% strength sodium hydroxide solution. The suspension is heated to about 50° C. and stirred at that temperature for 4 hours. After cooling 10% strength hydrochloric acid is added to adjust the pH to about 7. The resulting light yellow, clear solution can be used directly in the corresponding applications.

However, the brightener solution can also be repeatedly diafiltered to remove the excess of polyglycol 400 and the salts formed in the course of the reaction. Diafiltration and drying of the solution provides a light yellow solid.

Elemental analysis indicates a molecular formula of $C_{66}H_{93}N_{10}O_{32.5}S_4Na_4$, corresponding to the formula 1×1.5H$_2$O:

|  | C | H | N | O | S | Na |
|---|---|---|---|---|---|---|
| Found | 44.9 | 5.2 | 7.9 | 29.9 | 7.3 | 5.01 |
| Calculated | 44.9 | 5.3 | 7.9 | 29.9 | 7.3 | 5.2 |

The starting compound of the formula 2 is prepared in a conventional manner by reacting cyanuric chloride with 4,4'-diaminostilbene-2,2'-disulfonic acid and then with 4-aminobenzenesulfonic acid.

The compound of the formula 1 can also be successfully prepared by initially charging a suspension of 117 g of the compound of the formula (2) in 281 g of 7% strength sodium hydroxide solution and then adding 500 g of polyglycol 400 with stirring. This is followed by a three-hour reaction time at 30° C. Hydrochloric acid is added to adjust the pH into the neutral range.

It is similarly possible to initially charge a mixture of 117 g of the compound of the formula (2), 500 g of polyglycol 400 and 332 g of 15% strength aqueous sodium carbonate solution and then to let the reaction proceed at 100° C. for 6 hours. After cooling, the pH is adjusted to 7 by addition of hydrochloric acid.

Example 2

Preparation of a Compound of the Formula (3)

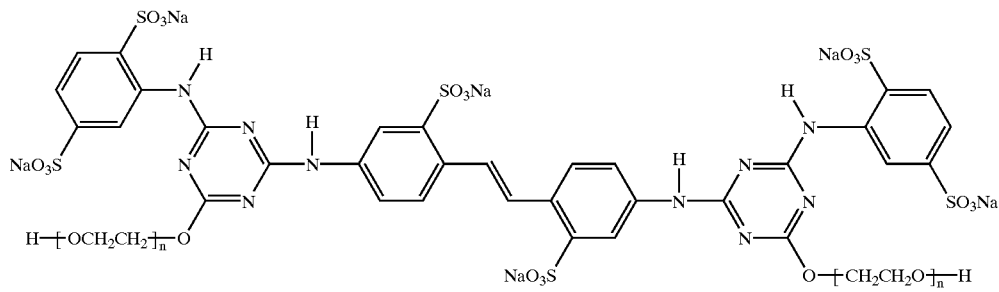

formula 3 n = 8.5

193 g of the compound of the formula 4

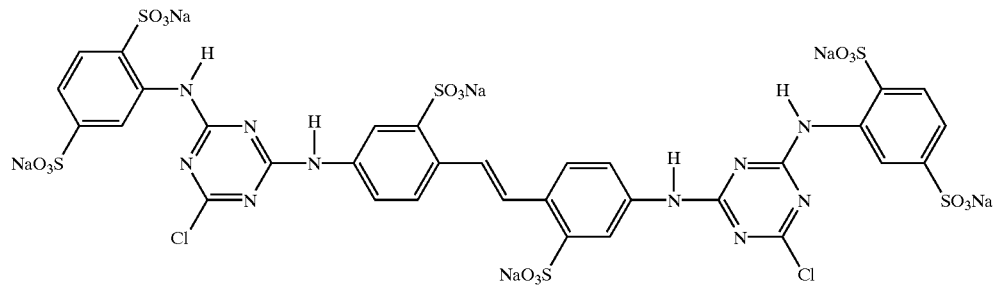

formula 4 are suspended in a mixture of 1000 g of polyglycol 400 and 360 g of 5% strength sodium hydroxide solution. The suspension is heated to about 50° C. and stirred at that temperature for 4 hours. After cooling 10% strength hydrochloric acid is added to adjust the pH to about 7.

The resulting light yellow solution can be used directly in the corresponding applications.

The starting compound of the formula 4 is prepared in a known manner by reacting cyanuric chloride with 4,4'-diaminostilbene-2,2'-disulfonic acid and 2,5-disulfoaminobenzene.

Example 3

Use in Paper Coating

A brightener- and wood-free DIN A4 base paper (basis weight 80 g/m$^2$) is coated on a laboratory doctor coating machine (from Erichsen, K-Control-Coater, model K 202) with a coating of the following composition:

60 parts calcium carbonate
40 parts of kaolin
10 parts of SBR latex
1 part of polyvinyl alcohol
0.25 part of polyacrylic acid The pH of the coating composition is adjusted to 8–8.5 with dilute aqueous sodium hydroxide solution. The solids content of the coating composition is adjusted to 60–65% by addition of water. This is followed by the addition of 11 g, based on 1 kg of coating composition, of compound of Example 1.

The sheets are dried in a drying cylinder at 95° C. for 1 min and then stored at 23° C. and a humidity of 50% for 3 hours before they are measured. The result is a paper having very good whiteness.

Example 4

Use in Paper Size Press

A brightener- and wood-free DIN A4 base paper (basis weight 80 g/m$^2$) is wetted on a laboratory size press (from Werner Matthis AG, TYPE No. HF 18374) with an aqueous liquor containing 50 g/l of starch and
1 g/l of compound of Example 1.

The liquor pH is 7. The wet pick-up is about 50–60%.

The sheets are subsequently dried in a drying cylinder at 95° C. for 1 min and then stored at 23° C. and a humidity of 50% for 3 hours before they are measured. The result is a paper having very good whiteness.

Example 5

Use on Cotton, Pad-dry Process

Scoured and bleached woven cotton fabric is padded on a laboratory pad-mangle with an aqueous liquor containing 14 g/l of compound of Example 1 and
3 g/l of sodium sulfate.

The liquor pick-up of the fabric is adjusted to about 80% by squeezing off between the pad-mangle rolls. This is immediately followed by drying of the fabric by a tenter pass at 100° C. for 30 seconds. This treatment provides a very good brightening effect on the material.

Example 6

Use on Cotton, Dry Crosslinking

Scoured and bleached cotton poplin is impregnated on a laboratory pad-mangle with an aqueous liquor of the following composition:

14 g/l of compound of Example 1
80 g/l of Fixapret® NF (product of BASF)
25 g/l of Condensol® N (product of BASF)

The fabric is squeezed off between rolls to a liquor pick-up of about 80% of the dry weight. This is followed by drying on a tenter at 100° C. for 30 seconds. Curing is likewise effected on a tenter, at 150° C. for 4 minutes.

This treatment provides a very good brightening effect on the material.

Example 7

Comparative Example Based on Prior Art in Paper Coating

The following two compounds are compared with each other in the manner described in Example 3:

a) prior art: (DE-A-23 35 570)

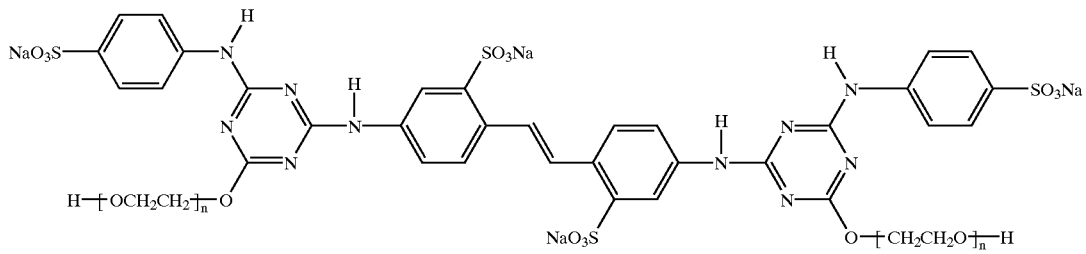

n = 3 b) compound of Example 1 according to the invention:

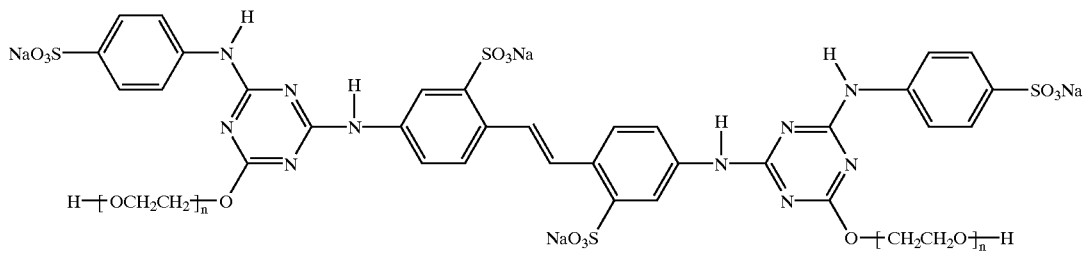

n = 8.5

The two samples are first adjusted to the same color strength by addition of water and then each admixed with 34% of polyethylene glycol 1500. To be able to assess the white build-up, the two samples are used in various concentrations, namely each at 0.4%, 0.8%, 1.6%, 2.4% and 3.2%, based on the solids content of the coating composition.

The table shows the whiteness measurement results of the papers thus prepared:

| CIELAB whiteness | Use level | | | | |
|---|---|---|---|---|---|
| | 0.4% | 0.8% | 1.6% | 2.4% | 3.2% |
| a) Prior art | 81.2 | 85.4 | 92.0 | 98.1 | 101.6 |
| b) Sample according to the invention | 81.4 | 86.9 | 94.4 | 100.0 | 103.6 |

It is clear that the use of the compound according to the invention provides enhanced whiteness compared with the prior art.

What is claimed is:
1. A compound of the formula (I)

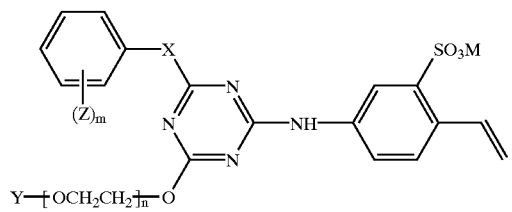
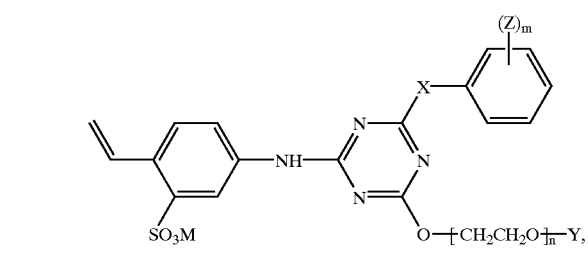

(I)

Where
Z is $SO_3M$, $COOR^1$, $CONR^1$, $SO_2NHR^1$, $NHCOR^1$, $COR^2$, or CN, where
$R^1$ is M or $C_1$–$C_3$-alkyl and
$R^2$ is $C_1$–$C_3$-alkyl or phenyl, X is O or $NR^3$, where
$R^3$ is hydrogen or $C_1$–$C_4$-alkyl,
Y is hydrogen or $C_1$–$C_4$-alkyl,
M is hydrogen, an alkali metal cation, or an optionally substituted ammonium ion,
n is from 7 to 35, and
m is 0, 1 or 2.

2. A compound of the formula (I) according to claim 1 wherein the radical of the formula

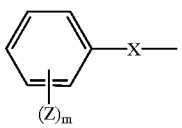

is derived from a compound of the formula (V)

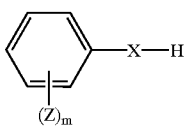

selected from the group consisting of phenol, phenolsulfonic acid, aniline, sulfanilic acid, and dimetanilic acid.

3. A compound according to claim 1 wherein
Z is $SO_3M$,
m is 0, 1, or 2,
X is NH,
n is from 7 to 15,
Y is hydrogen, and
M is hydrogen, Na, K, or $C_1$–$C_4$-mono-, -di-, -tri-, or -tetra-alkanolammonium.

4. A compound according to claim 1 wherein
Z is $SO_3M$,
m is 1,
X is NH,
n is from 7 to 15,
Y is hydrogen, and
M is Na or K.

5. A compound according to claim 1 conforming to the formula (II)

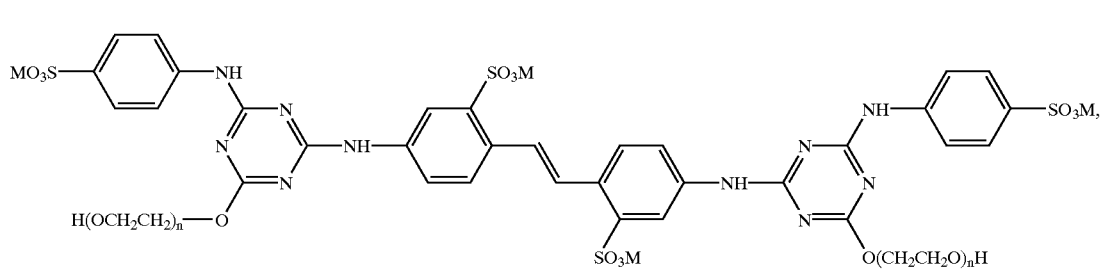

where
M is hydrogen, Na, or K, and
n is from 7 to 15.

6. A process for preparing a compound according to claim 1 comprising reacting a compound of the formula (III)

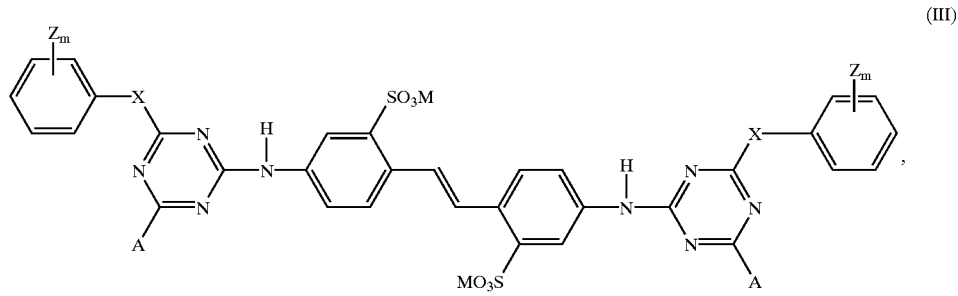

(III)

where
A is Cl or F,
Z is $SO_3M$, $COOR^1$, $CONR^1$, $SO_2NHR^1$, $NHCOR^1$, $COR^2$, or CN, where
$R^1$ is M or $C_1$–$C_3$-alkyl and
$R^2$ is $C_1$–$C_3$-alkyl or phenyl,
X is O or $NR^3$, where
$R^3$ is hydrogen or $C_1$–$C_4$-alkyl,
M is hydrogen, an alkali metal cation, or an optionally substituted ammonium ion, and
m is 0, 1 or 2,
with a compound of the formula (IV)

$$Y\text{—}O\text{—[}CH_2CH_2O\text{—]}_n H \qquad (IV)$$

where
Y is hydrogen or $C_1$–$C_4$-alkyl, and
n is from 7 to 35.

7. A brightener preparation comprising at least one compound according to claim 1 and a polyglycol ether.

8. A coating composition comprising
(1) 5 to 70% by weight of a white pigment, and
(2) 0.005 to 1% by weight, based on the white pigment, of a compound according to claim 1.

9. A method comprising brightening polyamide, cellulose, paper, or laundry detergent with a compound according to claim 1.

* * * * *